United States Patent [19]

Weiss et al.

[11] 4,002,915
[45] Jan. 11, 1977

[54] ASSEMBLY FOR TAKING A CONTINUOUS X-RAY PICTURE OF THE DENTAL ARCH

[75] Inventors: Charles M. Weiss, New York, N.Y.; Sadayasu Ota, Kyoto, Japan

[73] Assignee: Kabushiki Kaisha Morita Seisakusho, Japan

[22] Filed: Dec. 9, 1974

[21] Appl. No.: 531,071

[52] U.S. Cl. .............. 250/490; 250/523; 250/525; 250/320

[51] Int. Cl.² ......................... H01J 35/00

[58] Field of Search .......... 250/490, 491, 523, 525, 250/320

[56] References Cited

UNITED STATES PATENTS

| | | | |
|---|---|---|---|
| 1,120,748 | 12/1914 | Ryder | 250/523 |
| 2,281,931 | 5/1942 | Frank | 250/445 T |
| 3,536,913 | 10/1970 | Huchel | 250/490 |
| 3,617,742 | 11/1971 | Schulman et al. | 250/468 |
| 3,673,408 | 6/1972 | Moss | 250/490 |
| 3,806,731 | 4/1974 | Kataoka et al. | 250/490 |
| 3,806,732 | 4/1974 | Miyahara | 250/523 |
| 3,831,034 | 8/1974 | Ota et al. | 250/523 |
| 3,838,286 | 9/1974 | Prendergast et al. | 250/490 |

*Primary Examiner*—Alfred E. Smith
*Assistant Examiner*—Bruce C. Anderson

[57] ABSTRACT

The disclosure relates to improvements in an assembly for taking a continuous X-ray picture of the dental arch of a human being, wherein a support base is supported by a wall construction so as to be either vertically slidable or fixed in position, thereby utilizing space much more effectively and improving the appearance of the assembly, and eliminating for an operator or a patient any problem regarding movement of the feet on taking the X-ray picture.

6 Claims, 8 Drawing Figures

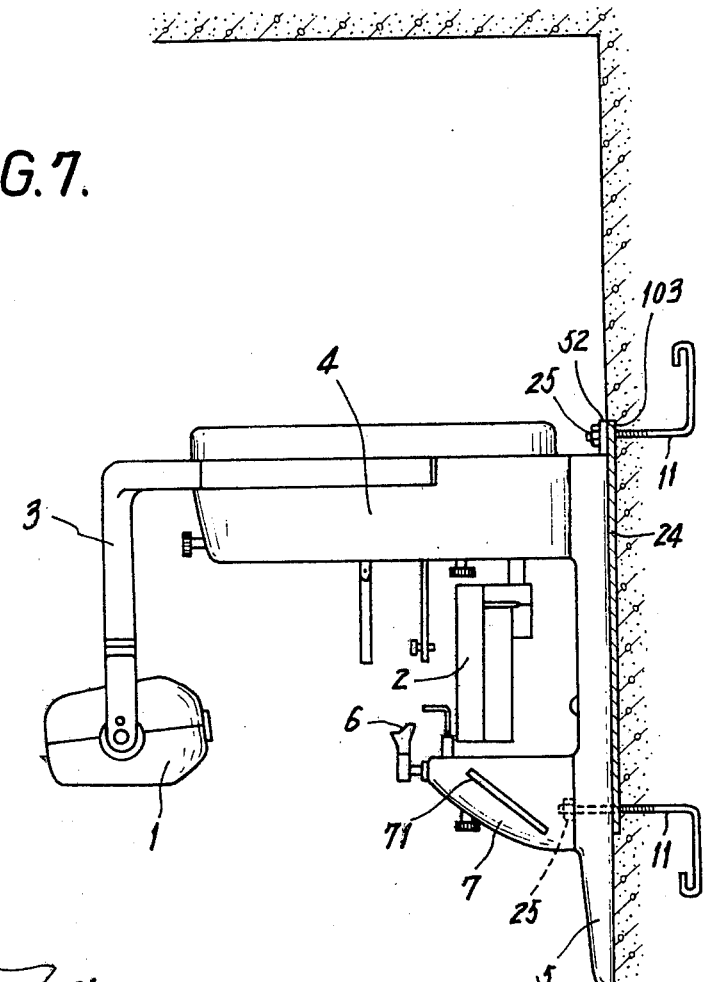
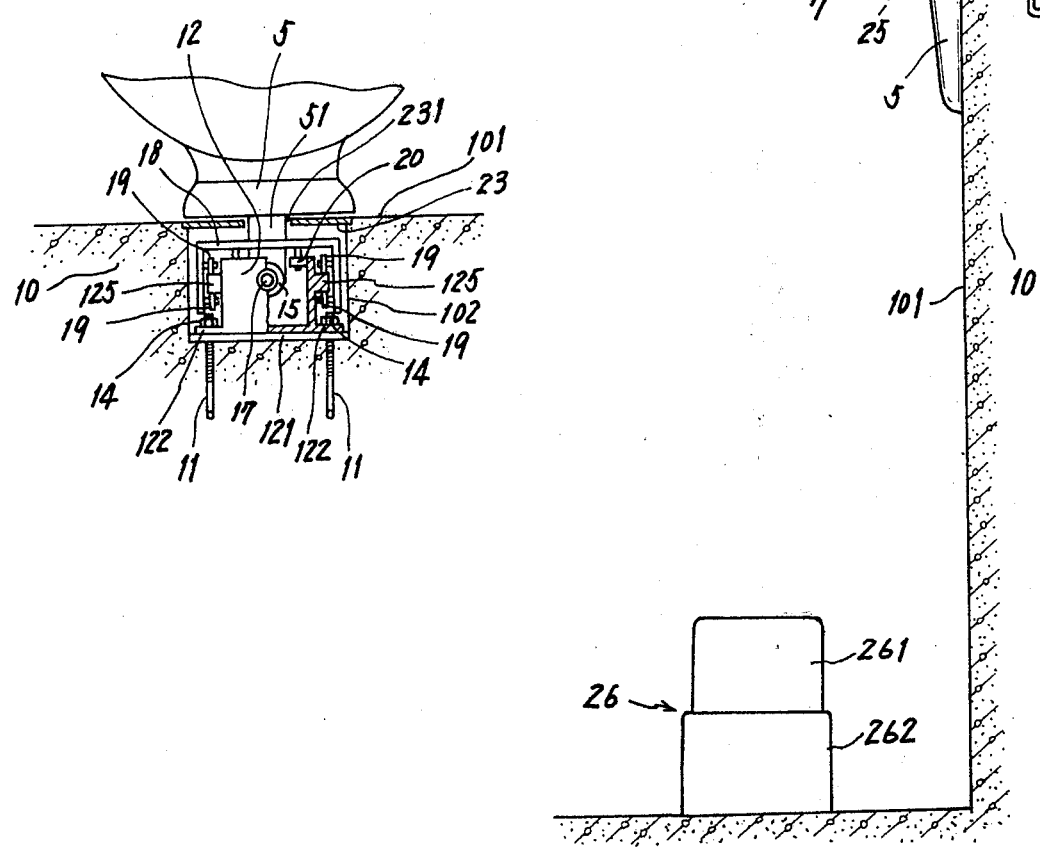
FIG. 7.
FIG. 6.

ASSEMBLY FOR TAKING A CONTINUOUS X-RAY PICTURE OF THE DENTAL ARCH

BACKGROUND OF THE INVENTION

This invention relates to improvements in an assembly for taking X-ray pictures of the dental arch of a human being which includes a X-ray tube and a film holder to be moved along the dental arch of a patient so as to take necessary X-ray pictures thereof, wherein a support base is supported by a wall construction so as to be vertically slidable or fixed in position.

An apparatus for taking a clear continuous X-ray picture of the dental arch of a patient is well known and the applicant of the present invention presented an effective apparatus of this kind in U.S. Pat. No. 3,831,034 or U.S. Pat. No. 3,806,732, wherein, since the dental arch approximately forms an elliptical arc, in order to take a continuous X-ray picture of the dental arch, a X-ray tube and a film holder are moved relatively to the dental arch so that the locus of movement of the X-ray tube and the film holder forms an elliptical arc during which a continuous X-ray picture is taken.

Heretofore, for taking a continuous X-ray picture of the dental arch of a patient in use of such an apparatus, there has conventionally been used a stand support type assembly slidable along the stand as is shown in FIG. 8. In FIG. 8, numeral 4 denotes a body which is provided therein with a mechanism for moving a X-ray source 1 and a film holder 2 in an elliptical path by means of an arm 3. A vertical support base 5 is extended from said body 4 and the lower portion of said support base 5 is provided with means for resting patient's jaw comprising a horizontal base 7 and a chin rest 6 secured thereto, and said support base is adapted to elevatably move along the stand post 8. The stand post 8 is supported securely with the lower end thereof by a stand base 9. In this construction, the operation mechanism of the X-ray source 1 and the film holder 2 housed in the body 4 includes a lot of structural members thereby making the body 4 high in weight and even slight vibration accompanied by the movement of the arm 3 may affect the photographic results. From the standpoints as such, the stand post 8 and the stand base 9 should be designed so large as to be rigid and stable thereby making the assembly relatively of large dimension. Consequently, the assembly occupies larger space in an examination room preventing utilization of space, making the room of ill appearance and also making it necessary for an operator or a patient to pay attention to their feet on taking X-ray pictures.

Accordingly, the primary object of the invention is to provide an assembly for taking a continuous X-ray picture of the dental arch of a human being which includes a X-ray tube and a film holder to be moved along said arch so as to take necessary X-ray picture, wherein a support base is supported by a wall construction so as to be vertically slidable or fixed in position thereby eliminating the stand post and the stand base from the assembly from which the above-mentioned disadvantages derived.

Another object of the invention is to provide for such assembly as aforesaid a simple mechanism for effecting support of the wall construction.

BRIEF DESCRIPTION OF THE DRAWINGS

These and other objects and advantages of the invention will become more apparent by reading the following description of several preferred embodiments thereof with reference to the accompanying drawings, wherein the same reference symbols in different figures denote corresponding parts, and wherein:

FIG. 6 is a sectional view taken on line VI—VI of FIG. 5;

FIG. 7 is a side elevational view partly in section of a fixed type of assembly according to the present invention.

DETAILED DESCRIPTION OF THE INVENTION

Figure 1:
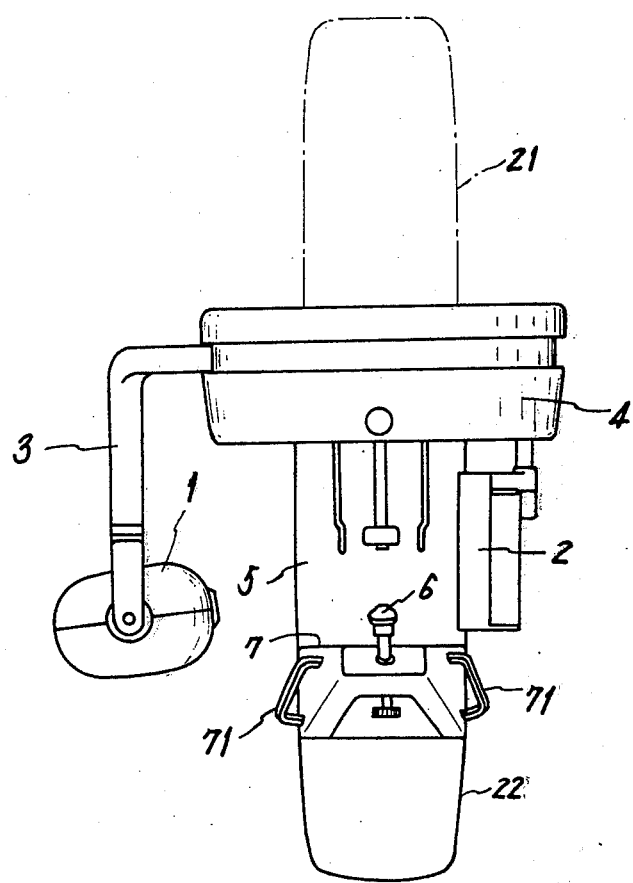
FIG. 1 is a plan view of an elevatable-projecting type of assembly for taking a continuous X-ray picture of the dental arch according to the present invention.

An assembly of wall support type for taking a continuous X-ray picture of the dental arch according to the invention comprises two types with respect to the mechanism as shown in the drawings, one of which has an elevatable mechanism between a support base and a wall construction in order that the support base is vertically slidable under the conditions that the support base is supported by the wall construction, and the other of which does not have such elevatable mechanism but the support base is fixedly supported by the wall construction. The former is to be referred to as an elevatable type and the latter a fixed type. The elevatable length of support base is designed at the average height difference of adults and for infants and juveniles, a fixed foot stand or an elevatable foot stand, if necessary, is further applied to the assembly.

Further, the elevatable mechanism in the case of the elevatable type is classified as a projecting type where the elevatable mechanism projects from the wall surface into a room and an embedded type where the elevatable mechanism is embedded in the wall construction so that the back surface of the support base is approximately in a same plane as the wall surface.

The former in which the elevatable mechanism is projecting or exposed is referred to as the projecting type and the latter in which the elevatable mechanisn is embedded is referred to as the embedded type.

On the other hand, the fixed type assembly has no such elevatable mechanisn as above-mentioned but the support base is disposed in contact with the wall surface.

Figure 4:
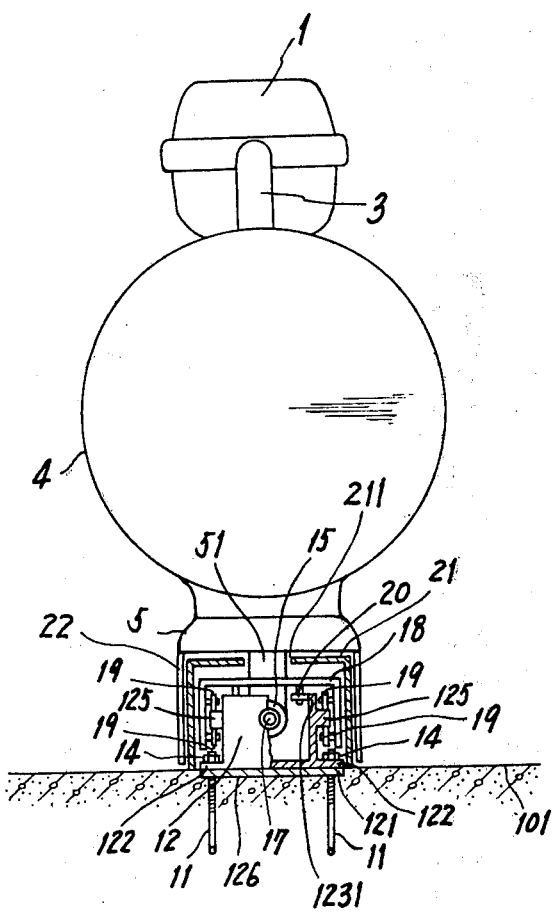
FIG. 4 is a sectional view taken on line IV—IV of FIG. 2.
Figure 5:
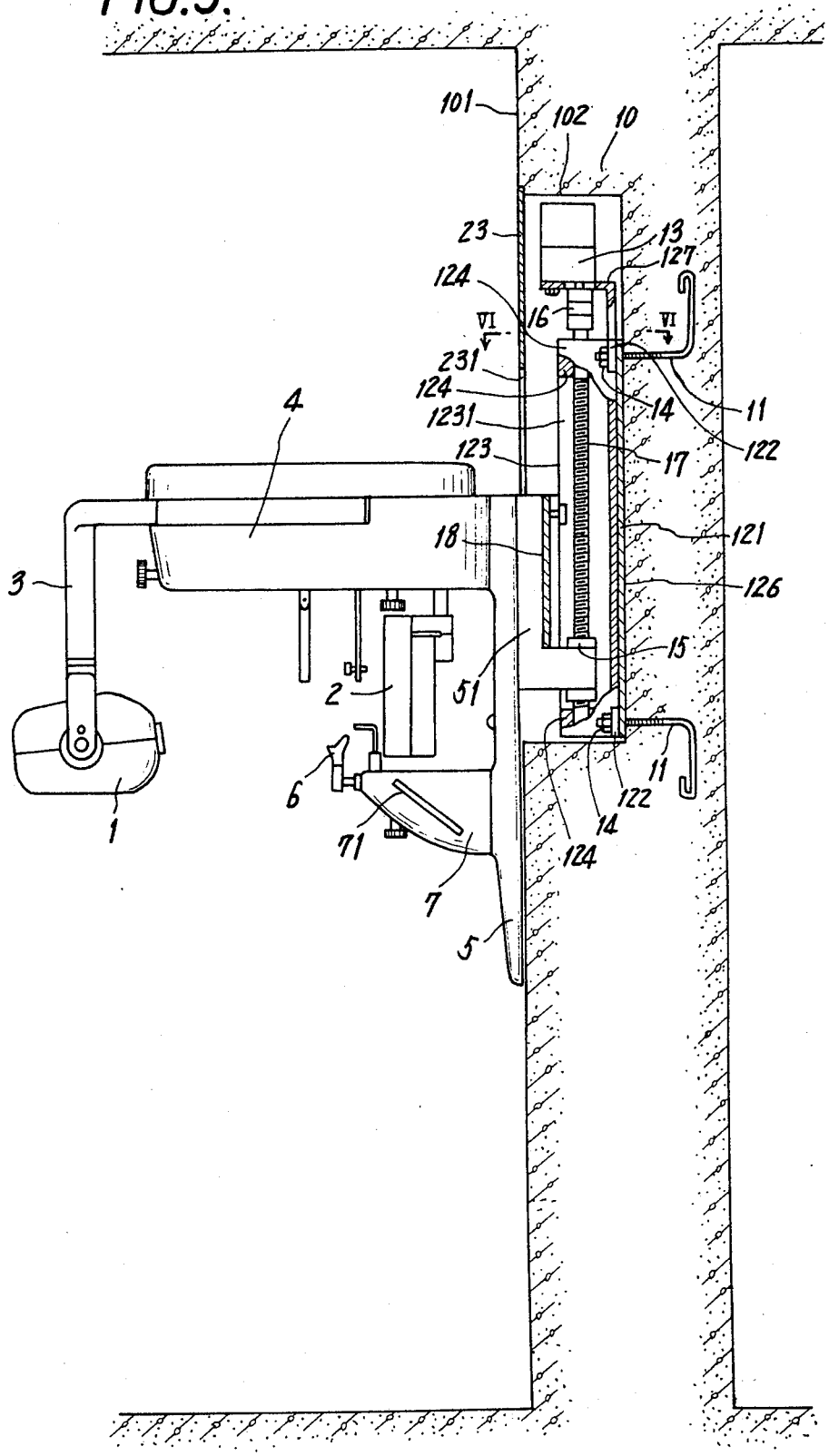
FIG. 5 is a side elevational view partly in section of an elevatable-embedded type of assembly according to the present invention in which the support base is in its lowermost position.
Figure 8:
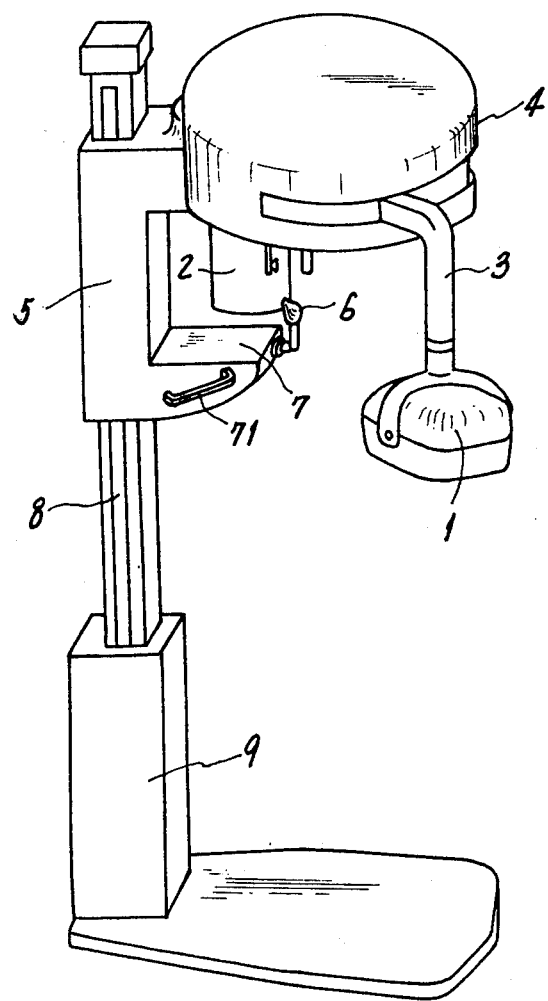
FIG. 8 is a schematic perspective view of a conventional assembly of a support post elevatable type.

The aforesaid FIG. 1 to FIG. 1 to FIG. 4 show an elevatable-projecting type, FIG. 5 and FIG. 6 shows an elevatable-embedded type and FIG. 7 illustrates a fixed type, respectively, and as for the wall construction, concrete is a preferred example.

These are now described in detail with reference to the drawings. In FIG. 1, a X-ray source 1 and a film holder 2 are disposed at both sides of the patient's head and source 1 is carried on an arm 3 at a longitudinally spaced position of the arm 3. A body 4 member houses therein a means for rotating said film holder 2 around said arm 3 and for simultaneously moving said X-ray source 1 and said film holder 2 about the patient's jaw. The mechanism for facilitating such operation, is shown in the above-mentioned U.S. Pat. No. 3,831,034 or U.S. Pat. No. 3,806,732 and requires no detailed description here.

In this example, the support base 5 and the connecting means embedded in the wall construction 10 are combined indirectly with the intermediate elevatable mechanism, whereby the elevatable mechanism projects from a wall surface 101 (FIG. 2) and anchor bolts 11 are shown as the connecting means. Each pair of anchor bolts 11 is embedded in respective upper and lower portions of the concrete wall construction. A box cap 12 has, at the back side thereof, a bolt-attaching flap 122 including a bolt hole at the position corresponding to the above-mentioned anchor bolt 11, at the upper end thereof, a support 127 to mount a motor 13 thereon, at the front side thereof, an opening guide 123 and through respective thickness of the upper and the lower walls of the box, bearings 124, 124. The box cap 12 is secured to the wall surface 101 in such a manner that the back side of the box cap 12 is contacted with a back plate 121 arranged in a recess 126 provided in the wall construction 10 and fastened by means of a nut 14 to the anchor bolt 11 at the bolt-attaching flap 122. The elevatable mechanism comprises a sleeve nut 15 fixed to the bottom end of a protruded seat 51 provided for the support base 5 at the wall side thereof (in the drawing, it is integrally extended from the protruded seat 51) and a screw-threaded rod 17 on which the nut 15 is fitted, said screw-threaded rod 17 being connected to a flexible shaft coupling 16 and rotatably held by the bearings 124, 124 in the cap 12 and driven by the motor 13. The elevatable mechanism further includes means for preventing crosswise vibrations produced on elevation of the support base 5. Namely, at the above-mentioned protruded seat 51 is provided a channel 18 of reverse U-shape for encircling the box cap 12. At the opposite inner sides of the channel 18 are provided respectively first pairs of guide rollers 19—19, 19—19 and at the front inner side of the channel 18 are provided a second pair of guide rollers 20—20. The vibration preventing is effected in such a manner that each first pair of guide rollers 19—19, 19—19 roll in contact with rails 125, 125 respectively provided at the front and the back sides of the box cap 12, while the above-mentioned second guide rollers 20—20 roll in contact with an internal wall 1231 of the aforesaid opening guide 123 at the front side of the box cap 12. In consideration of preventing poor appearance of the elevatable mechanism which is exposed in a room, a pair of up and down covers 21, 22 are provided along the wall surface 101 for covering the elevatable mechanism. The upper cover 21 is provided with a longitudinal opening guide 211 at the front side thereof for elevating the aforesaid protruded seat 51 and the lower cover 22 is secured to the support base 5 in order to slide, cooperating with the elevation of the support base 5, over the outside of the upper cover 21 in non-contact relationship thereto.

As is understood already, the elevation of the support base 5 of this embodiment is facilitated by the rotation of the screw-threaded rod 17 driven by the motor 13 thereby elevating the sleeve nut 15. Lowering of the support base 5 is carried out in opposite manner.

Figure 2:
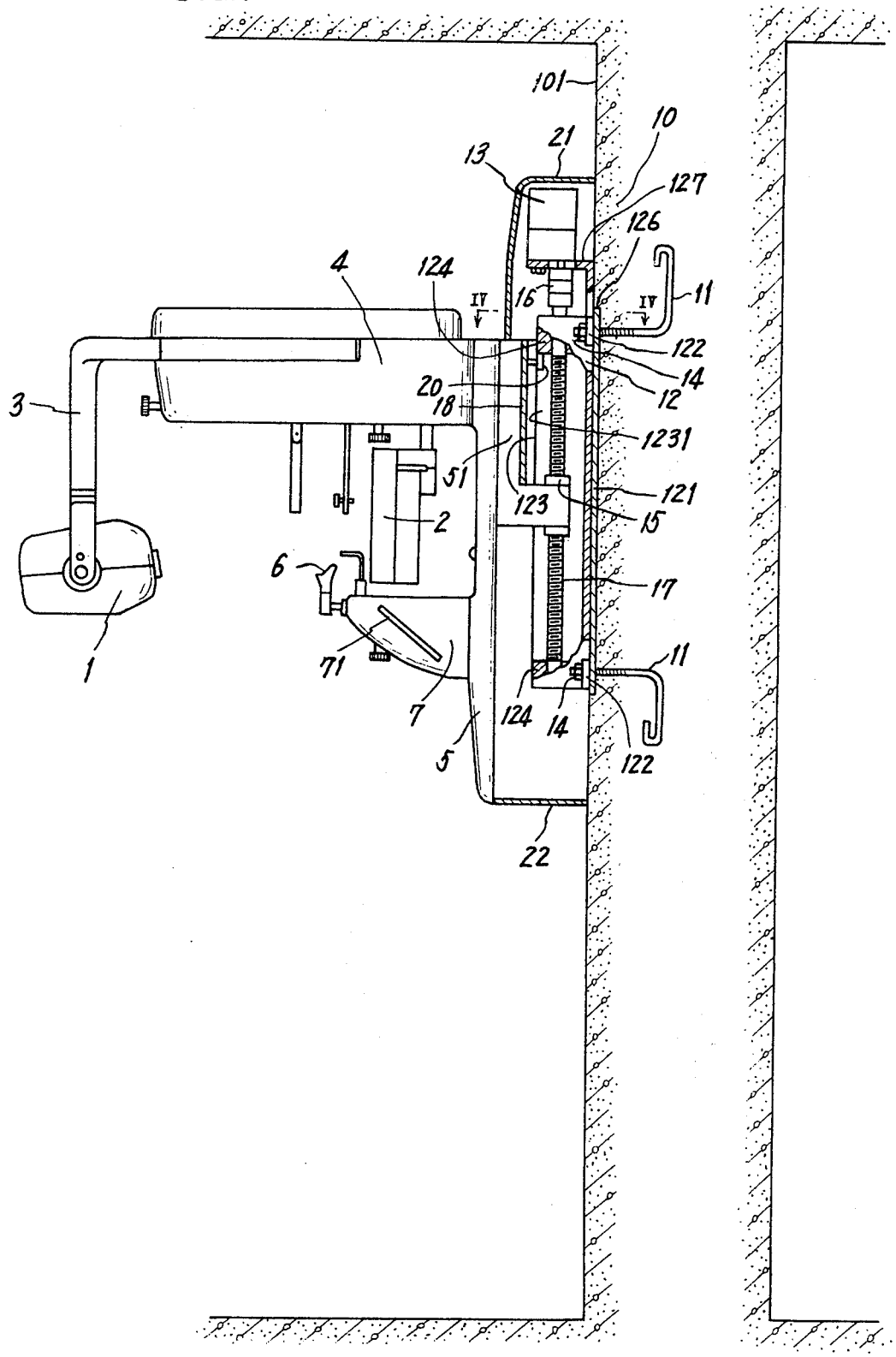
FIG. 2 is a side elevational view of FIG. 1 partly in section in which the support base is in its uppermost position.
Figure 3:
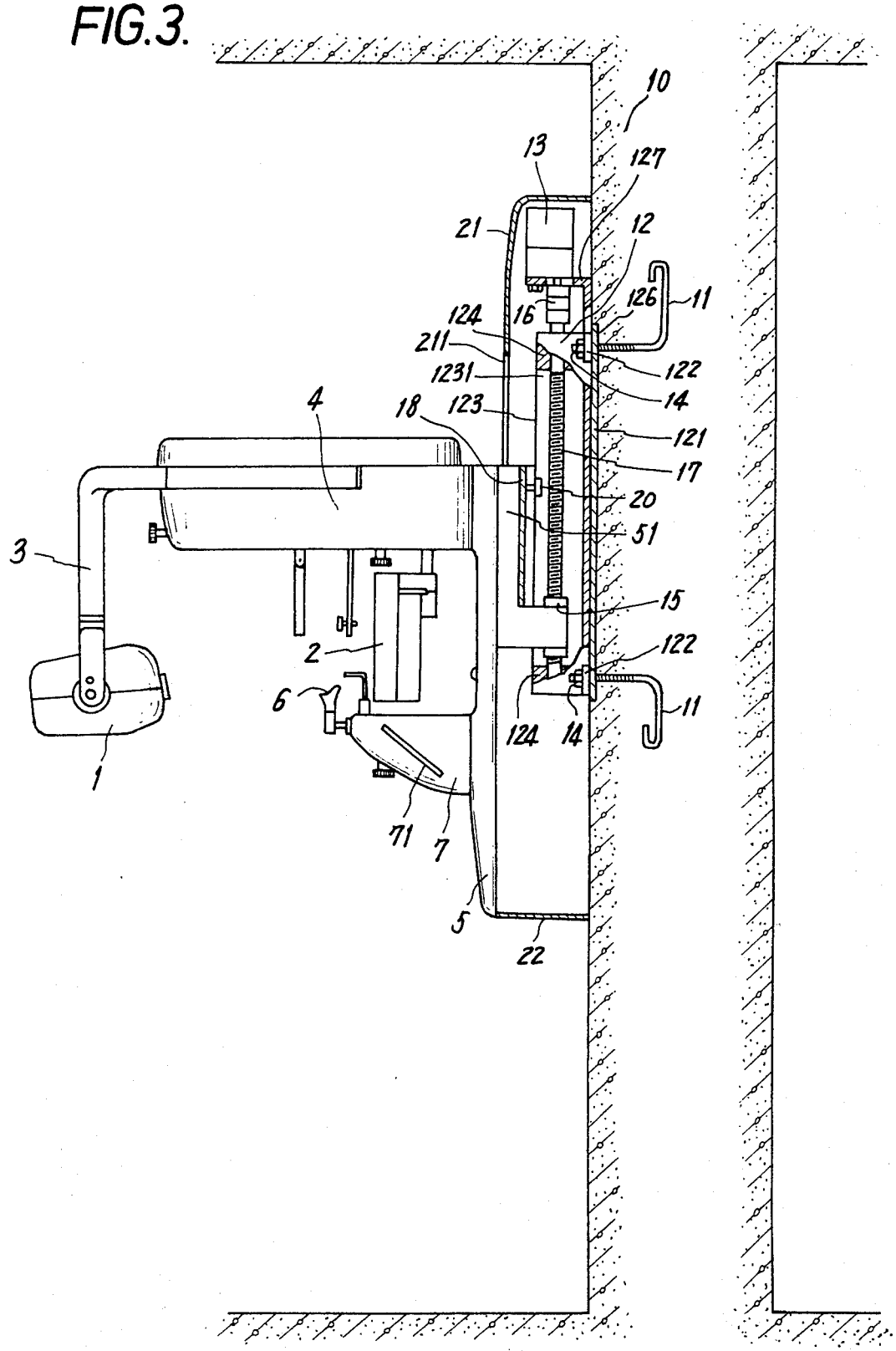
FIG. 3 is a side elevational view of FIG. 1 partly in section in which the support base is in its lowermost position.

In FIG. 1 and FIG. 2, the base support 5 is shown at its uppermost position and in FIG. 4 (and in the dotted line of FIG. 1), it is shown in its lowermost position, respectively. The elevation stroke of the base support 5 is set at the average height difference of adults, however, for infants or juvenile patients, a foot stand of an automatic elevatable type or a fixed type can be applied (not shown in FIG. 1 to FIG. 4).

The manner of taking a continuous X-ray picture of the dental arch is that the base support 5 is set in such a position by moving the elevatable mechanism that the chin of the patient may be comfortably mounted on the chin rest 6 at the standing posture of the patient, then hand grips 71 of the horizontal base 7 are held by both hands of the patient to maintain the position and thereafter the mechanism for operating the X-ray source 1 and the film holder 2 in the body 4 is driven, whereby the X-ray source 1 and the film holder 2, positioned at the opposite sides of the head of the patient, move along the dental arch. Thus, a continuous X-ray picture is taken. During the operation, the film holder 2 rotates in order to expose successively fresh sensitive surfaces to the X-ray source 1 so that a continuous X-ray picture can be obtained.

The embodiment of an elevatable-embedded type substituted for an elevatable-projecting type makes use of the same anchor bolts 11 and elevatable mechanism shown in FIG. 5 and FIG. 6. As is apparent from the drawings, in this embodiment, a recess 102 is provided at the wall construction 101 and the elevatable mechanism is housed in the wall recess 102. The support base 5 is arranged so that the back surface thereof may be approximately in a same plane as the wall surface 101. A flat laminated facing 23 having an opening guide 231 is substituted to be applied for the upper and lower covers 21, 22 in the previous embodiment.

The fixed type embodied in the present invention without the elevatable mechanism is shown in FIG. 7. In this embodiment, the support base 5 is directly connected with the anchor bolts 11. In detail, an anchor bolt-attaching flap 52 is provided to the support base 5 and also a shallow recess 103 is provided in the wall surface 101. In the recess 103 is embedded a back plate 24 in order to contact with the back surface of the support base 5. The anchor bolts 11 and the support base 5 are directly connected by means of the nuts 25 in such a manner that the forward end of the anchor bolt 11 is passed through the anchor bolt-attaching flap 52 through the back plate 24. Thus, in this type, the back surface of the support base 5 and the wall surface 101 are arranged so as to be in the same plane.

Furthermore in this embodiment, since the support base 5 is of fixed type, an elevatable foot stand 26 is necessary to be applied in order to make up for shortage of the patient's height. For this foot stand 26, a place-on floor type or a wall-attached type housing a suitable elevatable device may be adopted; however, in FIG. 7, a foot stand of a place-on floor type is shown comprising an upper and a lower piece 261, 262 in which the upper piece 261 is adapted to be elevatable with respect to the lower piece 262 by an interior elevatable device of pressure oil equipment.

As the present assembly already understood from the above embodiments, instead of the conventional support base which is elevated along the support post, the support base of the present invention is adapted to be supported elevatably or fixed in position by the wall construction, therefore utilization of space and good appearance are expected with recovering the space conventionally occupied by the support post or the stand base and there is no need for the operator or the patient to be concerned with the position or movement of their feet on taking X-ray pictures and further the construction is simple.

It is to be understood that the foregoing description is of preferred embodiments of the disclosed assembly and that various changes and modifications of the construction thereof may be made without departing from the spirit or scope of the following claims, in which modifications without departing from the spirit of the invention are, for instance;

1. Instead of the anchor bolts, to apply connecting means which are embedded in the wall construction used in an ordinary building construction such as a combination of an embedded channel and a connecting bolt.
2. To apply, for the wall construction, a mortar wall, composite wall of steel frame and panel for prefabricated structure or a mudwall for wooden houses.
3. To combine the connecting means with the elevatable mechanism or with the support base by means other than that of the above embodiments.
4. To apply a manual type winch mechanism including a drum, a wire and a balance weight or an oil pressure device used in the known support post elevatable type instead of the electrically driven elevatable mechanism.

What is claimed is:

1. In an apparatus for taking a continuous X-ray picture of the dental arch, comprising a support base carrying an X-ray source, a film holder, means for supporting the patient's jaw, and means for simultaneously moving the X-ray source and the film holder about the patient's jaw, the improvement which comprises the combination of a vertically extending support base; a vertical wall construction; means for mounting said vertical support base on said vertical wall construction out of contact with the floor, said mounting means and said vertical wall construction providing the sole vertical and horizontal support for said vertical support base; means for raising and lowering said support base, comprising a housing fixed to said mounting means, a vertical threaded rod in said housing, motor means for rotating said rod, and a sleeve nut means on said support base threadely engaging said rod and operable to raise or lower the support base upon rotation of said rod; and means for preventing transverse vibrations during elevation of the support base, comprising a vertically extending U-shaped channel member on said support base and disposed around said rod, opposed vertically extending rails mounted on said housing adjacent each leg of the channel member, each rail having three roller-engaging surfaces each parallel to the longitudinal axis of the rod, the first and second surfaces being parallel to the wall construction and the third surface being perpendicular to the wall construction, a pair of rollers mounted on each leg of said channel member and engaging said first and second surfaces of the adjacent rail and a pair of rollers mounted on the base of the U-shaped channel member and engaging the third surface of the adjacent rail.

2. Apparatus according to claim 1, wherein said housing is on a surface of the wall construction.

3. An assembly as claimed in claim 1, wherein said support base is constructed and arranged so that the back surface thereof is approximately in the same plane as said wall surface.

4. An assembly as claimed in claim 1, wherein said wall construction is made of concrete.

5. An assembly as claimed in claim 1, wherein said wall construction is selected from a mortar wall, a composite wall of steel frame and panel or a mud-wall for wood housing construction.

6. An assembly as claimed in claim 1, wherein said housing is in a recess in said wall construction.

* * * * *